(12) United States Patent
Buckley et al.

(10) Patent No.: US 11,786,356 B2
(45) Date of Patent: *Oct. 17, 2023

(54) BIASED ENDOLUMINAL DEVICE

(71) Applicant: W. L. Gore & Associates, Inc., Newark, DE (US)

(72) Inventors: Kyle R. Buckley, Flagstaff, AZ (US); Vincent L. Perko, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 198 days.

This patent is subject to a terminal disclaimer.

(21) Appl. No.: 16/836,190

(22) Filed: Mar. 31, 2020

(65) Prior Publication Data
US 2020/0289254 A1    Sep. 17, 2020

Related U.S. Application Data

(63) Continuation of application No. 13/330,522, filed on Dec. 19, 2011, now Pat. No. 10,617,514.

(60) Provisional application No. 61/425,882, filed on Dec. 22, 2010.

(51) Int. Cl.
*A61F 2/07* (2013.01)
*A61F 2/89* (2013.01)
*A61F 2/95* (2013.01)

(52) U.S. Cl.
CPC .............. *A61F 2/07* (2013.01); *A61F 2/9526* (2020.05); *A61F 2/89* (2013.01); *A61F 2/9522* (2020.05); *A61F 2002/072* (2013.01); *A61F 2002/075* (2013.01); *A61F 2230/005* (2013.01); *A61F 2230/0019* (2013.01); *Y10T 29/49863* (2015.01)

(58) Field of Classification Search
None
See application file for complete search history.

(56) References Cited

U.S. PATENT DOCUMENTS

| | | | |
|---|---|---|---|
| 3,953,566 A | 4/1976 | Gore | |
| 4,187,390 A | 2/1980 | Gore | |
| 4,503,569 A | 3/1985 | Dotter | |
| 4,512,338 A | 4/1985 | Balko et al. | |
| 4,990,155 A | 2/1991 | Wilkoff | |

(Continued)

FOREIGN PATENT DOCUMENTS

| | | | |
|---|---|---|---|
| JP | 2003-505144 A | 2/2003 | |
| JP | 2005-514968 A | 5/2005 | |

(Continued)

OTHER PUBLICATIONS

International Preliminary Report on Patentability received for PCT Patent Application No. PCT/US2011/065989, dated Jul. 4, 2013, 5 pages.

(Continued)

*Primary Examiner* — Leslie Lopez

(57) ABSTRACT

An endoluminal device can comprise a flexible tubular wall and a frame member. The frame member can be comprised of a shape-memory material having sides with protrusions which are partially or substantially flattened when formed together with the flexible tubular wall to thereby create a bias in the side wall of the endoluminal device that resists deformation from a desired device profile during crush loading and is thereby resistant to invaginations when deployed.

14 Claims, 2 Drawing Sheets

(56) References Cited

U.S. PATENT DOCUMENTS

| | | | |
|---|---|---|---|
| 5,037,427 | A | 8/1991 | Harada et al. |
| 5,147,370 | A | 9/1992 | McNamara et al. |
| 5,211,658 | A | 5/1993 | Clouse |
| 5,221,261 | A | 6/1993 | Termin et al. |
| 5,276,276 | A | 1/1994 | Gunn |
| 5,922,019 | A | 7/1999 | Hankh et al. |
| 6,042,602 | A | 3/2000 | Wells |
| 6,086,610 | A | 7/2000 | Duerig et al. |
| 6,110,198 | A | 8/2000 | Fogarty et al. |
| 6,120,534 | A | 9/2000 | Ruiz |
| 6,139,573 | A | 10/2000 | Sogard et al. |
| 6,203,735 | B1 | 3/2001 | Edwin et al. |
| 6,327,772 | B1* | 12/2001 | Zadno-Azizi ............ A61F 2/88 29/557 |
| 6,336,937 | B1 | 1/2002 | Vonesh et al. |
| 6,352,561 | B1 | 3/2002 | Leopold et al. |
| 6,355,057 | B1* | 3/2002 | DeMarais ................ A61F 2/91 623/1.15 |
| 6,366,937 | B1 | 4/2002 | Shridhar et al. |
| 6,395,212 | B1 | 5/2002 | Solem |
| 6,551,350 | B1 | 4/2003 | Thornton et al. |
| 6,613,077 | B2 | 9/2003 | Gilligan et al. |
| 6,635,083 | B1 | 10/2003 | Cheng et al. |
| 6,729,356 | B1 | 5/2004 | Baker et al. |
| 6,773,454 | B2 | 8/2004 | Wholey et al. |
| 6,899,727 | B2 | 5/2005 | Armstrong et al. |
| 6,981,982 | B2 | 1/2006 | Armstrong et al. |
| 7,049,380 | B1 | 5/2006 | Chang et al. |
| 7,731,744 | B1 | 6/2010 | Cox |
| 8,048,138 | B2 | 11/2011 | Sullivan et al. |
| 10,617,514 | B2 | 4/2020 | Buckley et al. |
| 2001/0039446 | A1 | 11/2001 | Edwin et al. |
| 2001/0049550 | A1 | 12/2001 | Martin et al. |
| 2001/0053929 | A1* | 12/2001 | Vonesh .................... A61F 2/07 623/1.12 |
| 2002/0007955 | A1 | 1/2002 | Wiens |
| 2002/0177891 | A1 | 11/2002 | Parodi |
| 2004/0063805 | A1 | 4/2004 | Pacetti et al. |
| 2005/0049667 | A1 | 3/2005 | Arbefeuille et al. |
| 2006/0052865 | A1 | 3/2006 | Banas |
| 2006/0198866 | A1 | 9/2006 | Chang et al. |
| 2007/0250153 | A1* | 10/2007 | Cully ....................... A61F 2/07 623/1.13 |
| 2008/0039927 | A1 | 2/2008 | Barr |
| 2008/0071356 | A1 | 3/2008 | Greenhalgh et al. |
| 2008/0288044 | A1 | 11/2008 | Osborne |
| 2009/0048662 | A1 | 2/2009 | Pavcnik et al. |
| 2012/0323304 | A1 | 12/2012 | Buckley et al. |
| 2013/0131780 | A1 | 5/2013 | Armstrong et al. |
| 2015/0005870 | A1 | 1/2015 | Kovach et al. |
| 2019/0388214 | A1 | 12/2019 | Silverman et al. |

FOREIGN PATENT DOCUMENTS

| | | |
|---|---|---|
| JP | 2007-503923 A | 3/2007 |
| WO | 97/33532 A2 | 9/1997 |
| WO | 98/26731 A2 | 6/1998 |
| WO | 01/06953 A1 | 2/2001 |
| WO | 01/24733 A1 | 4/2001 |
| WO | 2002/100297 A2 | 12/2002 |

OTHER PUBLICATIONS

International Preliminary Report on Patentability received for PCT Patent Application No. PCT/US2018/015736, dated Aug. 15, 2019, 7 pages.

International Search Report and Written Opinion received for PCT Patent Application No. PCT/US2011/065989, dated Jun. 26, 2012, 7 pages.

International Search Report and Written Opinion received for PCT Patent Application No. PCT/US2018/015736, dated Apr. 17, 2018, 10 pages.

* cited by examiner

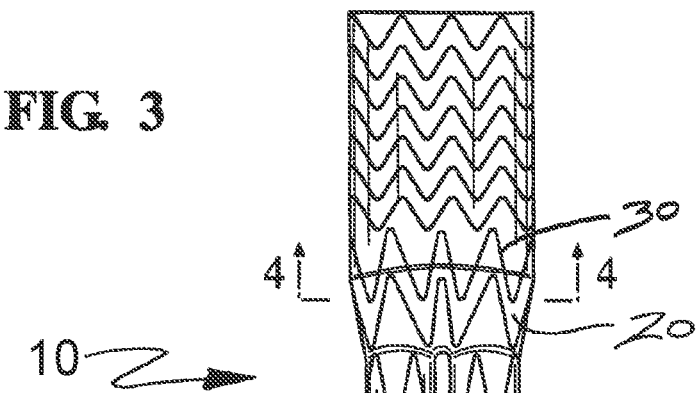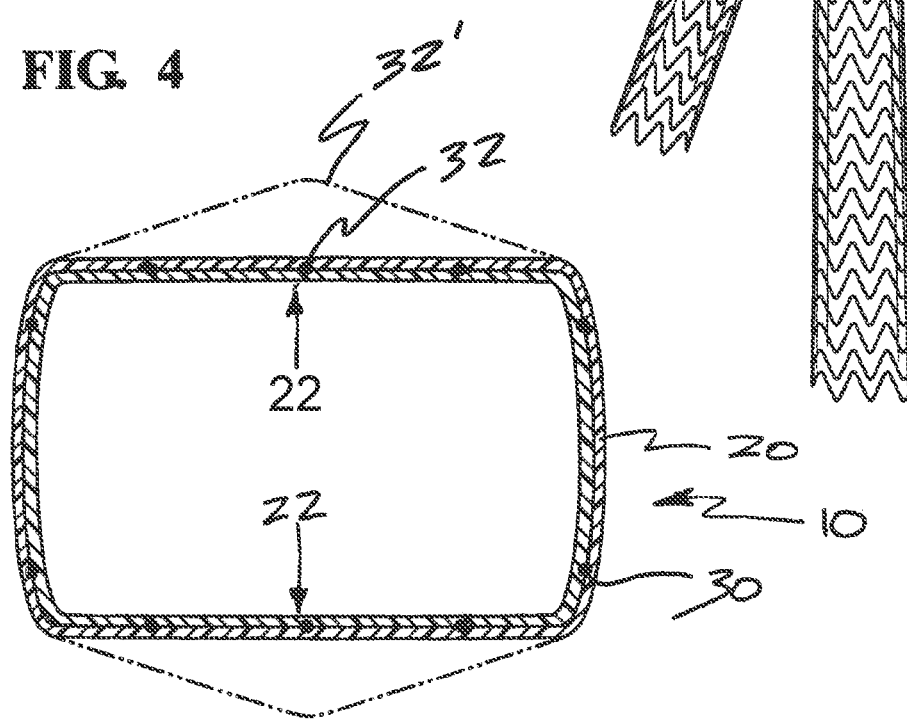

BIASED ENDOLUMINAL DEVICE

CROSS REFERENCE TO RELATED APPLICATIONS

This application is a Continuation of U.S. Ser. No. 13/330,522, filed Dec. 19, 2011, now U.S. Pat. No. 10,617,514, issued Apr. 14, 2020, which is a non-provisional of, and claims priority to, U.S. Provisional Patent Application No. 61/425,882, entitled "Deployment of Endoluminal Devices," filed Dec. 22, 2010, the contents of which are hereby incorporated by reference in their entireties.

BACKGROUND

Field

The present disclosure relates to improved expandable endoluminal devices for treating disease of the vasculature.

Discussion of the Related Art

To facilitate delivery to a treatment site, an expandable endoluminal device (e.g., a stent graft) can be crush loaded over a tubular element and retained by a sheath or other tubular element. Once delivered through the tortuous vasculature, deployment of the endoluminal device from the delivery device occurs at the treatment site.

Crushing can, in some instances, result in infolds in or invagination of the endoluminal device, especially where its cross sectional profile is not curved, as is sometimes the case in a bifurcation portion or an otherwise tapered portion.

It remains desirable to provide endoluminal devices that are resistant to infolding or invagination during crushing, as well as methods for making the same.

BRIEF DESCRIPTION OF THE DRAWINGS

In the following drawings:

FIG. 3 illustrates a front elevational view of an endoluminal device in accordance with various embodiments.

FIG. 4 is a cross-sectional of the endoluminal device in FIG. 3, in accordance with various embodiments, illustrating outward structural bias for resisting deformation during crushing and deployment.

DETAILED DESCRIPTION

Figure 1:
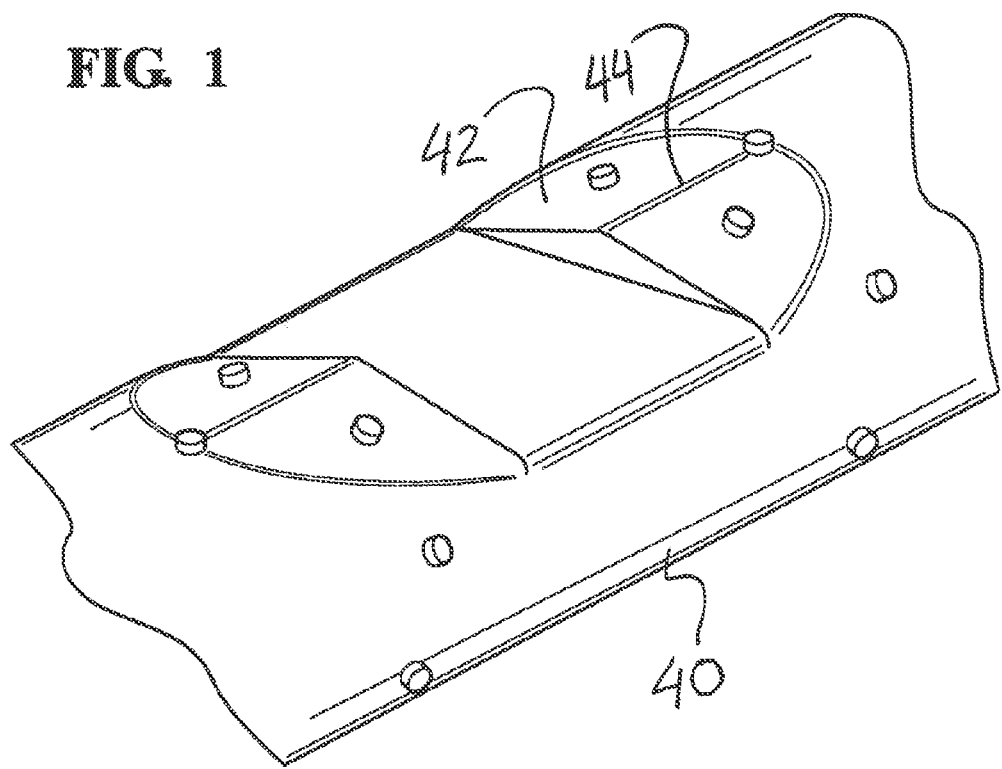
FIG. 1 illustrates in accordance with various embodiments a mandrel for forming a wire stent or frame member for endoluminal devices.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

An endoluminal device, in accordance with various embodiments, comprises a flexible tubular wall and a frame member having a bias for resisting deformation of the tubular wall, such as infolding or invagination, from a desired profile.

An endoluminal device, in accordance with various embodiments, can be any stent graft comprising a portion with a cross sectional profile having a desired profile and a structural bias that maintains the desired cross sectional profile of the device, for example, during deployment of the device along tortuous anatomy.

An endoluminal device, in accordance with various embodiments, can, for example, have a substantially uncurved section in a bifurcation portion or an otherwise tapered portion where the stent graft transitions from a larger perimeter to a smaller perimeter.

In various embodiments, a frame member includes a stent suitable for the treatment of vascular conditions, such as an abdominal aortic aneurism, and can provide structural support for the flexible tubular wall of the endoluminal device and/or the vasculature. A frame member can be comprised either of a wire have a helical configuration or be comprised of one or a plurality of rings. Among other configurations, the wire or a ring itself can be linear or have a sinusoidal or zig-zag pattern. Still other various embodiments of the frame member can be cut from a tube and have any pattern suitable for the treatment.

In various embodiments, the frame member comprises a shape-memory material, such as nitinol. In various embodiments, the frame member can be comprised of other materials, self-expandable or otherwise expandable (e.g., with a balloon or spring mechanism), such as various metals (e.g., stainless steel), alloys and polymers.

In various embodiments, a frame member includes one or more protrusions for creating a bias when the frame member is assembled with and/or between graft layers to form the endoluminal device. In general, a protrusion includes any elevation, ridge, projection, recession, indentation or other outwardly or inwardly extending feature that, while not assembled with a graft layer and/or between graft layers, is substantially different vis-a-vis the endoluminal device.

In various embodiments, the protrusion can be characterized by the frame member defining a lumen comprising a portion (e.g., a peripheral or an intermediate portion) having a cross-sectional area larger or smaller than that of the corresponding portion of the flexible tubular wall and/or the endoluminal device. The cross-sectional shape can be a pentagon, octagon or any other suitable shape.

In various embodiments, the frame member is configured to have convex or outwardly extending protrusions. However, a protrusion can be generally configured in any direction an internal structural bias is desired in the endoluminal device.

Protrusions can be manufactured into the frame member or otherwise introduced post manufacture. In various embodiments, a suitable bias can be achieved by a protrusion that is from about 5% to about 25% of a desired diameter or width of the flexible tubular wall and/or the endoluminal device. An endoluminal device can, for example, be made with a frame member having a protrusion that is about 10% of the diameter or width of the flexible tubular wall and/or endoluminal device, Generally, a larger protrusion dimension relative to the desired diameter or width of the flexible tubular wall and/or endoluminal device results in a higher bias for resisting infolding or invagination of the endoluminal device at or near the protrusion.

In various embodiments, a flexible tubular wall is generally any abluminal and/or luminal covering configured to partially or substantially smooth, flatten, or otherwise lessen the frame member protrusion and thereby bring the frame member protrusion into conformity with the desired dimension and profile of the endoluminal device.

In various embodiments, the shape of the frame is generally conical and is constrained toward a substantially cylindrical shape by the flexible tubular wall. In various embodiments, a flexible tubular wall defines a surface that does not include a protrusion present in the frame member. In various embodiments, a portion of a flexible tubular wall (e.g., a peripheral or an intermediate portion) has a cross-sectional area that does not include protrusion present in the corresponding portion of the frame member.

In various embodiments, a flexible tubular wall comprises taped ePTFE. Other useful materials for the flexible tubular wall can comprise one or more of nylons, polycarbonates, polyethylenes, polypropylenes, polytetrafluoroethylenes, polyvinyl chlorides, polyurethanes, polysiloxanes, and other biocompatible materials.

In various embodiments, a flexible tubular wall is fixedly secured or otherwise coupled at a single or a plurality of locations to the abluminal or luminal surface of the frame member, for example, using heat shrinking, adhesion or other processes known in the art. In various embodiments, the flexible tubular wall is coupled to an anchor extending outwardly from the frame and being generally proximal to the frame protrusion. In various embodiments, a plurality of flexible tubular walls are used, the walls being coupled to both the abluminal and luminal surfaces of the frame member.

Various embodiments comprise one or more flexible tubular walls that are coupled to the frame member at, along or near the frame member protrusion to partially or substantially smooth, flatten, or otherwise lessen the frame member protrusion and thereby create an internal structural bias in the direction of the protrusion when the device is in an unconstrained state.

In various embodiments, frame member protrusion is partially or substantially flattened when coupled to or otherwise formed together with the flexible tubular wall. Flattening the protrusion of the frame member can create a structural bias in the endoluminal device that resists radial deformation (e.g., infolding or invagination) in a direction substantially opposite the protrusion, or that otherwise resists deformation from its cross-sectional shape, during crush loading and maintains its structural integrity when deployed and the device is in an unconstrained state.

In various embodiments, the endoluminal device has a resistance to radial deformation which varies circumferentially or peripherally about a cross section generally normal to a longitudinal axis of its lumen. The resistance can peak at a middle portion where one or more flexible tubular walls are coupled to the frame member.

In various embodiments, methods for making a biased endoluminal device can comprise forming the frame member on a first mandrel having a surface that includes one or more protrusions as compared to the desired profile of the endoluminal device at or near the protrusion. The endoluminal device can then be formed by wrapping the flexible tubular wall about the frame member on a second mandrel not including the protrusions and subsequently heat shrinking the flexible tubular wall to the frame member.

An exemplary endoluminal device can thereafter be radially crush loaded with a reduced likelihood of there being undesired deformation, such as infolding or invagination. A supporting balloon can be introduced into the lumen of the endoluminal device and deflated during radial crush loading to further minimize any likelihood unwanted deformation.

Various embodiments of the present disclosure are described with reference to FIGS. 1, 2, 3 and 4. Specifically, with reference to FIG. 1, a mandrel 40 for forming a frame member, such as a stent, is provided having a tapered portion 42 where the device transitions from a larger perimeter to a smaller perimeter. Tapered portion 42 can comprise a 0.05 inch ridge protrusion 44, for example. However, smaller or larger protrusions, as well as differently shaped protrusions, can be used depending on the frame shape and amount of structural bias desired.

Figure 2:
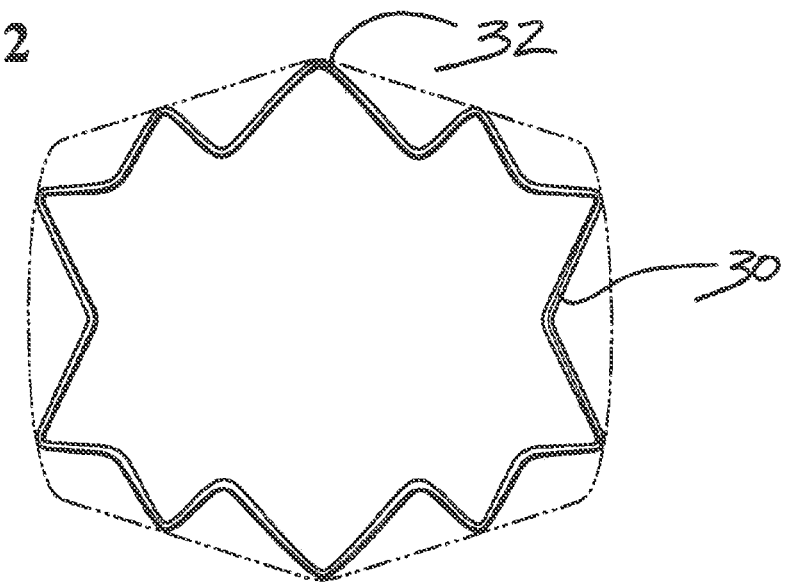
FIG. 2 illustrates an end view of a stent or frame member in accordance with various embodiments.

A nitinol stent frame member 30 is wound over mandrel 40, thus creating a corresponding 0.05 inch ridge protrusion 32 in the tapered portion of frame member 30, as shown illustratively in the end view of FIG. 2. Frame member 30 is then wrapped with an ePTFE flexible tubular wall 20 to flatten ridge protrusion 32. The resulting endoluminal device 10 is shown in FIGS. 3 and 4. For ease of comparison, the dotted line 32' in FIG. 4 illustrates the profile of the frame member assembled with a graft layer and/or between graft layers to form the device. Thus, it should be readily appreciated that the difference in profiles or positions between the unconstrained frame member 32' prior to device assembly and the frame member along the protrusion 32 after assembly with a graft layer and/or between graft layers generally represents a structural bias that resists infolding or invagination of the device along the portion of the frame member having the protrusion.

Endoluminal device 10 can be radially crush loaded with a radial crusher. Because of the internal structural bias (depicted as reference numeral 22 in FIG. 4) provided by the protrusion 32, the tapered portion resists inward deflection under the squeezing force of the radial crusher. Endoluminal device 10 is then retained by a sheath or other tubular element, delivered through the tortuous vasculature and deployed at the treatment site with no infolding or invagination.

Stents having protrusions for creating a structural bias the resists deformation of an endoluminal device from a desired profile, in accordance with various embodiments, can be fabricated, for example, from cut tubes, wound wires (or ribbons) or flat patterned sheets rolled into a tubular form. Stents can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stents can also comprise bioresorbable materials such as poly(amino acids), poly(anhydrides), poly(caprolactones), poly(lactic/glycolic acid) polymers, poly(hydroxybutyrates) and poly(orthoesters).

Potential materials for a graft member include, for example, expanded polytetrafluoroethylene (ePTFE), polyester, polyurethane, fluoropolymers, such as perfluoroelastomers and the like, polytetrafluoroethylene, silicones, urethanes, ultra high molecular weight polyethylene, aramid fibers, and combinations thereof. One preferred embodiment for a graft material is ePTFE. Other embodiments for a graft member material can include high strength polymer fibers such as ultra high molecular weight polyethylene fibers (e.g., Spectra®, Dyneema Purity®, etc.) or aramid fibers (e.g., Technora®, etc.). The graft member can include a bioactive agent. In one embodiment, an ePTFE graft includes a carbon component along a blood contacting surface thereof.

Typical materials used to construct catheters for endoluminal delivery of devices, as discussed above, can comprise commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE),Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluoroethylene (ECTFE), Ethylene, Ethylene Tetrafluoroethylene (ETFE), Polychlorotrifluoroethylene (PCTFE), Polytetrafluoroethylene (PTFE), Polyvinylidene Fluoride (PVDF), Perfluoroalkoxy (PFA). Other commonly known medical grade materials include elastomeric organosilicon polymers, polyether block amide or thermoplastic copolyether (PEBAX) and metals such as stainless steel and nickel/titanium alloys.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An endoluminal device having an abluminal surface and a luminal surface and including a smaller diameter configuration and a larger diameter deployed configuration, the endoluminal device comprising:
    a frame member having a generally frustoconical shape; and
    a flexible tubular wall configured to couple or secure to the frame member to constrain the frame member from the generally frustoconical shape to a substantially cylindrical shape to create an internal structural bias relative to the luminal surface that resists inward deflection in response to transition to the smaller diameter configuration;
    wherein the frame member has an outward bias when in the frustoconical shape such that one or more protrusions project radially outward from a remainder of the frame when the frame is in an unconstrained state, the one or more protrusions being compressed radially inwardly and secured toward a cylindrical shape through coupling of the flexible tubular wall to the frame member such that the frame member is in a constrained state; and
    wherein the outward bias of the frame member in the constrained state exhibits an increased internal structural bias in a direction of the one or more protrusions of the frame member as defined in the unconstrained state.

2. The device of claim 1, wherein the flexible tubular wall is fixedly secured or coupled to the frame member at a single or a plurality of locations along the abluminal or the luminal surface of the frame member.

3. The device of claim 1, wherein the internal structural bias resists infolding or invagination of the device along a portion of the frame member having the one or more protrusions.

4. The device of claim 1, wherein the flexible tubular wall includes one or more flexible tubular layers that are coupled to the frame member at, along or near the one or more protrusions to partially or substantially smooth, flatten, or lessen the one or more protrusions to the substantially cylindrical shape.

5. The device of claim 4, wherein the internal structural bias is a resistance to radial deformation that varies circumferentially or peripherally about a cross-section generally normal to a longitudinal axis of the luminal surface.

6. The device of claim 5, wherein the resistance is at a maximum at a middle portion of the frame member where the one or more flexible tubular layers are coupled to the frame member.

7. The device of claim 1, wherein the one or more protrusions includes at least one of elevations, ridges, projections, recessions, indentations or outwardly extending features relative to the frame member in the substantially cylindrical shape.

8. The device of claim 1, wherein the frame member is configured to resist the inward deflection relative to the luminal surface in response to a squeezing force of a radial crusher transitioning the frame member and the flexible tubular wall to the smaller diameter configuration.

9. The device of claim 8, wherein the frame member is configured to resist inward deflection and maintain the substantially cylindrical shape.

10. A device for treatment of vascular conditions, the device comprising:
    an endoluminal device having a smaller diameter configuration and a deployed configuration, the endoluminal including:
        a frame member having an outward bias in a configuration having one or more protrusions spaced about a perimeter of the frame member that project radially outward from a remainder of the frame when the frame is in an unconstrained state, wherein the remainder of the frame comprises at least one additional protrusion and
        a flexible tubular wall configured to couple or secure to the frame member to constrain the one or more protrusions radially inwardly to a substantially cylindrical shape such that the frame member is in a constrained state, wherein the outward bias of the frame member in the constrained state exhibits an increased structural bias that resists deflection of the device in a direction opposite that of the one or more protrusions as defined in the unconstrained state in response to transition to the smaller diameter configuration;
a sheath configured to maintain the device in the smaller diameter configuration and deploy the device to the deployed configuration without infolding or invagination.

11. The device of claim 10, wherein the structural bias resists the infolding or invagination of the device along a portion of the frame member having the one or more protrusions.

12. The device of claim 10, wherein the structural bias is a resistance to radial deformation that varies circumferentially or peripherally about a cross-section generally normal to a longitudinal axis of a luminal surface of the device.

13. The device of claim 12, wherein the resistance is at a maximum at a middle portion of the frame member where one or more flexible tubular layers are coupled to the frame member.

14. The device of claim 10, wherein the frame member is configured to resist the inward deflection in the direction opposite of the one or more protrusions in response to a squeezing force of a radial crusher transitioning the frame member and the flexible tubular wall to the smaller diameter configuration.

* * * * *